(12) United States Patent
Tatti et al.

(10) Patent No.: US 9,096,908 B2
(45) Date of Patent: Aug. 4, 2015

(54) **SELECTIVE DETECTION OF *BORDETELLA* SPECIES**

(75) Inventors: Kathleen M. Tatti, Lawrenceville, GA (US); Kansas Sparks, Lenoir City, TN (US); M. Lucia Tondella, Decatur, GA (US)

(73) Assignee: The United States of America as Represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 81 days.

(21) Appl. No.: 13/266,099

(22) PCT Filed: Apr. 26, 2010

(86) PCT No.: PCT/US2010/032408
§ 371 (c)(1),
(2), (4) Date: Nov. 10, 2011

(87) PCT Pub. No.: WO2010/124281
PCT Pub. Date: Oct. 28, 2010

(65) Prior Publication Data
US 2012/0183959 A1    Jul. 19, 2012

Related U.S. Application Data

(60) Provisional application No. 61/172,382, filed on Apr. 24, 2009.

(51) Int. Cl.
*C12Q 1/68* (2006.01)
*C12P 19/34* (2006.01)

(52) U.S. Cl.
CPC ............... *C12Q 1/689* (2013.01); *C12Q 1/686* (2013.01)

(58) Field of Classification Search
None
See application file for complete search history.

(56) References Cited

U.S. PATENT DOCUMENTS

| 6,261,785 B1 | 7/2001 | Wood et al. |
| 7,427,404 B1 * | 9/2008 | Pizza et al. ................. 424/240.1 |
| 2004/0265853 A1 | 12/2004 | Cockerill et al. |

FOREIGN PATENT DOCUMENTS

| WO | 02/061141 A1 | 8/2002 |
| WO | 2009/055239 A1 | 4/2009 |

OTHER PUBLICATIONS

Antila et al. *Bordetella holmesii* DNA is not detected in nasopharyngeal swabs from Finnish and Dutch patients with suspected pertussis. J Med Microbiol 2006;55:1043-51.*
Buck et al. Design strategies and performance of custom DNA sequencing primers. BioTechniques 1999;27:528-36.*
Koidl et al. Detection and differentiation of *Bordetella* spp. by real-time PCR. J Clin Microbiol 2007;45(2):347-50.*
Julian Parkhill et al; Comparative analysis of the genome sequences of *Bordetella pertussis, Bordetella parapertussis* and *Bordetella bronchiseptica*; Nature Genetics; vol. 35; No. 1; Sep. 2003; XP-002319843; pp. 32-40.
Lynne M. Sloan et al.; Multiplex LightCycler PCR Assay for Detection and Differentiation of *Bordetella pertussis* and *Bordetella parapertussis* in Nasopharyngeal Specimens; Journal of Clinical Microbiology; pp. 96-100, 2002.
Kate E. Templeton et al.; Evaluation of Real-Time PCR for Detection of and Discrimination between *Bordetella pertussis, Bordetella parapertussis*, and *Bordetella holmesii* for Clinical Diagnosis; Journal of Clinical Microbiology; pp. 4121-4126, 2003.

* cited by examiner

*Primary Examiner* — Young J Kim
(74) *Attorney, Agent, or Firm* — Gifford, Krass, Sprinkle, Anderson & Citkowski, P.C.; Weston R. Gould

(57) ABSTRACT

A process for detecting *Bordetella* spp. nucleic acid in a biological sample includes producing an amplification product(s) by amplifying one or more *Bordetella* spp. in a multiplex single chamber PCR assay, and measuring the amplification product(s) to detect or distinguish *Bordetella* spp. in the biological sample. Also provided are reagents and methods for detecting and distinguishing *Bordetella* spp. from each other and other bacteria or viruses. A kit is provided for detecting and quantifying one or more *Bordetella* spp. in a biological sample.

9 Claims, 2 Drawing Sheets

SELECTIVE DETECTION OF *BORDETELLA* SPECIES

CROSS-REFERENCE TO RELATED APPLICATION

Figure 1:
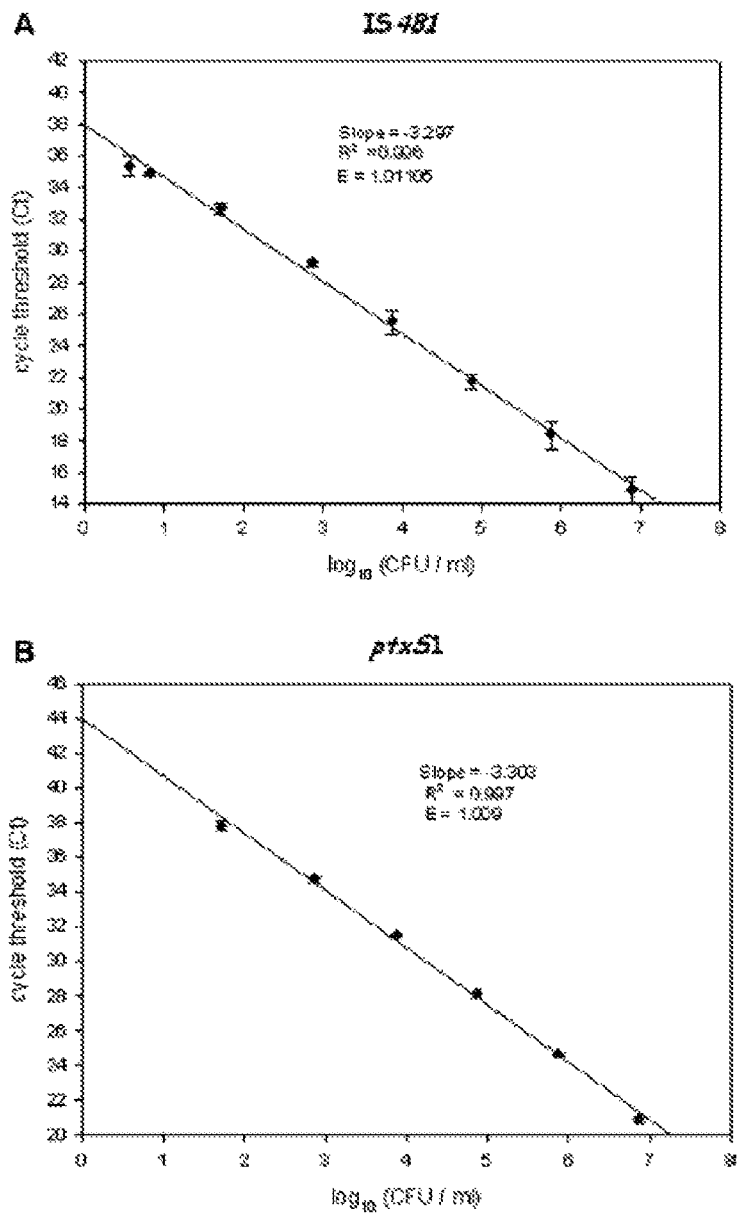
Figure 2:
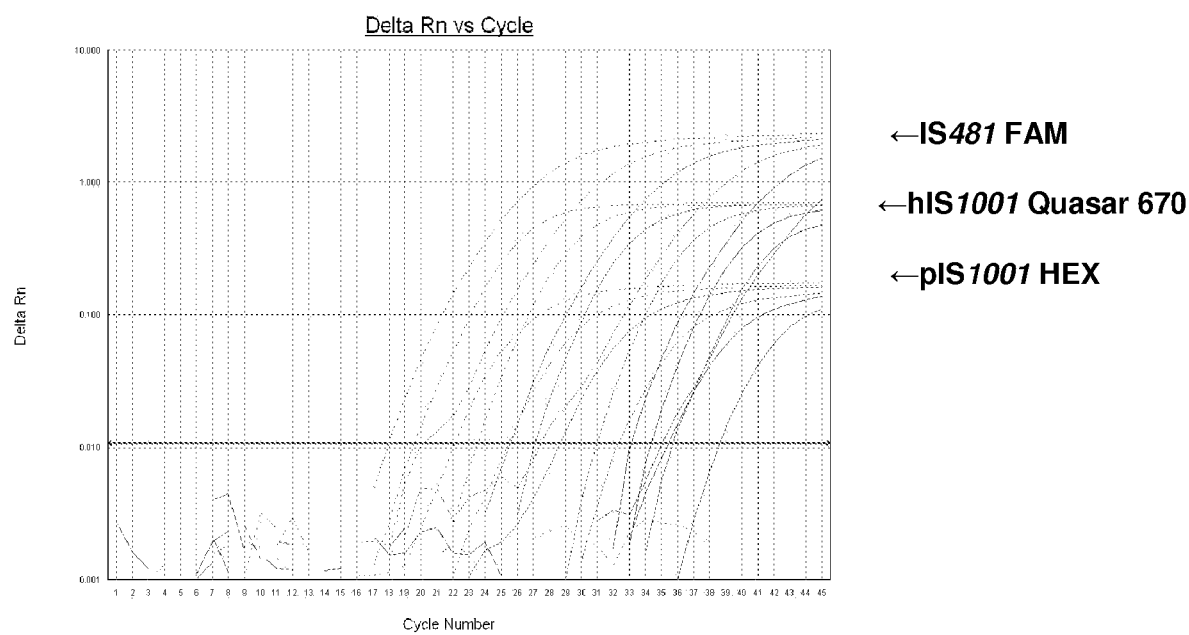

This application is the United States national stage of PCT/US2010/032408 filed Apr. 26, 2010, which claims priority of U.S. Provisional Patent Application Ser. No. 61/172,382 filed Apr. 24, 2009, which is incorporated herein by reference.

FIELD OF THE INVENTION

This invention relates generally to processes for detection of bacteria in fluid samples, and in particular to selective detection of *Bordetella* sp. in biological or other fluid media. Processes are described for rapid, sensitive, and specific multiplex detection and differentiation of *B. pertussis, B. parapertussis*, and *B. holmesii* in human and animal biological samples and quantification thereof. Diagnostic kits are provided for detection and differentiation of *Bordetella* sp. in a clinical, laboratory, or field setting.

BACKGROUND OF THE INVENTION

*Bordetella pertussis*, the etiologic agent of whooping cough, is a substantial cause of morbidity and infant mortality worldwide. The majority of the estimated annual 279,000 infant pertussis deaths occur in developing countries (WHO, 2005). In the United States, 25,616 cases of pertussis were reported during 2005 (Kretsinger et al., *MMWR Recomm. Rep.* 55:1-44, 2006). The three most common *Bordetella* human upper respiratory pathogens are *B. pertussis, B. parapertussis*, and *B. holmesii*. Others of the nine known species include *Bordetella bronchiseptica, Bordetella hinzii*, and *Bordetella trematum*. The *B. parapertussis* infection is less severe than *B. pertussis*, with symptoms that include a paroxysmal cough and a whoop that, if present, persists for a shorter duration (Mattoo and Cherry, *Clin. Microbiol. Rev.* 18:326-382, 2005). *B. holmesii* was first associated with septicemia in immunocompromised patients (Weyant et al., *J. Clin. Microbiol.* 33:1-7, 1995) and has been recovered from nasopharyngeal specimens of patients with pertussis-like diseases in Massachusetts (Yih et al., *Emerg. Infect. Dis.* 5:441-443, 1999). Therefore, differentiating these three species is essential to providing an accurate diagnosis of pertussis-like diseases or whooping cough in patient populations.

Prior art diagnostic methods to detect *B. pertussis* include culture, singleplex real-time polymerase chain reaction (PCR), and serology. Culture is 100% specific; however, it suffers from low sensitivity (12-60%) and lengthy incubation periods from 5 to 10 days (Wendelboe and Van Rie, *Expert Rev. Mol. Diagn.* 6:857-864, 2006). The sensitivity of culture is highest in young infants tested after a short duration of symptoms and the lowest in adolescents and adults tested after a longer duration of symptoms (Riffelmann et al., *J. Clin. Microbiol.* 43:4925-4929, 2005).

In the United States, the number of reported adult and adolescent pertussis cases has substantially increased in the last two decades; however, most cases are not laboratory confirmed, highlighting the need for additional diagnostic tests with higher sensitivity than culture. Although the lengthy incubation period for culture makes it impractical as a rapid diagnostic test, culture in combination with PCR is a reliable option for case detection during a public health response to a pertussis outbreak (Sotir et al., *Clin. Infect. Dis.* 44:1216-1219, 2007). Serologic assays are reviewed in detail elsewhere (Broder et al., 2006; Centers for Disease Control and Prevention [CDC], MMWR 56:837-842, 2007; Fry et al., *J. Med. Microbiol.* 53:519-525, 2004; Kretsinger et al., 2006; Mattoo and Cherry, 2005; Sotir et al., 2007).

Real-time PCR assays, which can be rapid (2-24 h), specific (86-100%), and sensitive (70-99%), have been designed to detect *B. pertussis* (Wendelboe and Van Rie, 2006). Conventional PCR assays introduced in 1989 (Houard et al., *Res. Microbiol.* 140:477-487, 1989) for the detection of *B. pertussis* are being replaced by real-time PCR assays in clinical diagnostics. However, standardizing these PCR methods is challenging (Arber, *FEMS Microbiol. Rev.* 24:1-7, 2000; Broder et al., *MMWR Recomm. Rep.,* 55:1-50, 2006; CDC, MMWR 53:216-219, 2004; Douglas et al., *J Med Microbiol* 38:140-144, 1993; Fry et al., 2004). Several chromosomal regions have been used as targets, such as adenylate cyclase (Douglas et al., 1993), pertactin (Byrne and Slack, *BMC Infect. Dis.* 6:53-61, 2006; Makinen et al., *Emerg. Infect. Dis.* 7:952-958, 2001; Vincart et al., *J. Med. Microbiol.* 42:847-849, 2007), porin (Li et al., *J. Clin. Microbiol.* 32:783-789, 1994; Qin et al., *J. Clin. Microbiol.* 45:506-511, 2007), recA (Antila et al., *J. Med. Microbiol.* 55:1043-1051, 2006; Qin et al., 2007; Vielemeyer et al., *J. Clin. Microbiol.* 42:847-849, 2004), pertussis toxin promoter region (Houard et al., *Res. Microbiol.* 140:477-487, 1989; Knorr et al., *BMC Infec. Dis.* 6:62-74, 2006; Makinen et al., 2001; Nygren et al., *J. Clin. Microbiol.* 38:55-60, 2000; Reizenstein, *Dev. Biol. Stand.* 89:247-254, 1997; Stefanelli et al., *Diag. Microbiol. Infect. Dis.* 24:197-200, 1996), and, most frequently, insertion sequence IS481 (Glare et al., *J. Clin. Microbiol.* 28:1982-1987, 1990; McPheat and McNally, *J. Gen. Microbiol.* 133:323-330, 1987a, *FEMS Microbiol. Lett.* 41:357-360, 1987b; Templeton et al., *J. Clin. Microbiol.* 41:4121-4126, 2003; van der Zee et al., *J. Clin. Microbiol.* 31:2134-2140, 1993).

Accurate identification of pertussis cases in respiratory disease outbreaks is of particular importance because some interventions, such as vaccination, are pathogen specific. PCR confirmation is included in the case definition of pertussis from the Council of State and Territorial Epidemiologists. A confirmed case of pertussis is any person with acute cough illness of any duration with isolation of *B. pertussis*, or a case that meets the clinical case definition and is confirmed by PCR, or a case that meets the clinical definition and is epidemiologically linked directly to a case confirmed by either culture or PCR (Broder et al., 2006; Kretsinger et al., 2006). However, in respiratory disease outbreaks, positive results with a single PCR assay targeting the insertion sequence IS481 have led to a false diagnosis of pertussis, demonstrating the need for different or additional target (CDC, 2007; Farrell et al., *J. Clin. Microbiol.* 38:4499-4502, 2000; Lievano et al., *J. Clin. Microbiol.* 40:2801-2805, 2002; Muyldermans et al., *J. Clin. Microbiol.* 43:30-35, 2005).

Thus, there is a need for a rapid, sensitive, and discriminatory assay for detection of *Bordetella* sp. in complex clinical or laboratory samples in the presence or absence of other bacterial or viral agents.

SUMMARY OF THE INVENTION

A composition including an isolated nucleotide sequence of one or more of SEQ ID NOS: 1-12 or modifications of any thereof is provided herewith. The composition is operative to provide a rapid, sensitive, and selective detection of *Bordetella* species. The composition is useful as a uniplex or multiplex detection test. A kit is provided with a set of primers and a probe for specific detection of *B. pertussis, B. holmesii, B. parapertussis*, or sensitive to *B. pertussis/B. parapertussis* yet insensitive to *B. holmesii*.

A kit is provided to perform a process of detection and distinguishment between one or more *Bordetella* species in a biological sample that includes exposing the sample to forward primers of SEQ ID NOS: 1, 4 and 7 as well as reverse primers of SEQ ID NO: 2, 5 or 8 under conditions suitable for polymerase chain reaction to measure respective amplification products therewith indicative of *B. pertussis, B. holmesii* or *B. parapertussis*, respectively. Such a process is amenable to operation in a multiplex mode. The kit and the process it performs provides rapid diagnosis of *Bordetella* infection.

BRIEF DESCRIPTION OF THE DRAWINGS

FIGS. 1A and 1B are assay plots for IS481 (A) and PtxS1 (B) sequences, both showing linear application over orders of magnitude; and FIG. 2 is a plot of a multiplex assay for different strains of *B. pertussis.*

DETAILED DESCRIPTION OF THE PREFERRED EMBODIMENTS

The high incidence of false diagnosis of *Bordetella* infection combined with the highly species specific vaccines available makes diagnosing and distinguishing *Bordetella* species in suspect patients paramount for controlling outbreaks. The instant invention has utility for detection and distinguishing of *Bordetella* species in biological samples, diagnosis of disease associated therewith, and discrimination against other bacterial and viral pathogens. It is appreciated that an inventive process is readily performed for financial compensation.

The following definitional terms are used throughout the specification without regard to placement relative to these terms.

As used herein, the term "variant" defines either a naturally occurring genetic mutant of *Bordetella* or a recombinantly prepared variation of *Bordetella*, each of which contain one or more mutations in its genome compared to the *Bordetella* of *B. pertussis, B. parapertussis*, or *B. holmesii*. The term "variant" may also refer to either a naturally occurring variation of a given peptide or a recombinantly prepared variation of a given peptide or protein in which one or more amino acid residues have been modified by amino acid substitution, addition, or deletion.

As used herein, the term "analog" in the context of a non-proteinaceous analog defines a second organic or inorganic molecule that possesses a similar or identical function as a first organic or inorganic molecule and is structurally similar to the first organic or inorganic molecule.

As used herein, the term "derivative" in the context of a non-proteinaceous derivative defines a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated. A derivative also defined as a degenerate base mimicking a C/T mix such as that from Glen Research Corporation, Sterling, Va., illustratively LNA-dA or LNA-dT, or other nucleotide modification known in the art or otherwise.

As used herein, the term "mutant" defines the presence of mutations in the nucleotide sequence of an organism as compared to a wild-type organism.

As used herein, the term "hybridizes under stringent conditions" describes conditions for hybridization and washing under which nucleotide sequences having at least 30%, 35%, 40%, 45%, 50%, 55%, 60%, 65%, 70%, 75%, 80%, 85%, 90%, or 95% identity to each other typically remain hybridized to each other. Such hybridization conditions are described in, for example but not limited to, Current Protocols in Molecular Biology, John Wiley & Sons, NY (1989), 6.3.1 6.3.6.; Basic Methods in Molecular Biology, Elsevier Science Publishing Co., Inc., NY (1986), pp. 75 78, and 84 87; and Molecular Cloning, Cold Spring Harbor Laboratory, NY (1982), pp. 387 389, and are well known to those skilled in the art. A preferred, non-limiting example of stringent hybridization conditions is hybridization in 6× sodium chloride/sodium citrate (SSC), 0.5% SDS at about 68° C. followed by one or more washes in 2×SSC, 0.5% SDS at room temperature. Another preferred, non-limiting example of stringent hybridization conditions is hybridization in 6×SSC at about 45° C. followed by one or more washes in 0.2×SSC, 0.1% SDS at 50 to 65° C.

An "isolated" or "purified" nucleotide or oligonucleotide sequence is substantially free of cellular material or other contaminating proteins from the cell or tissue source from which the nucleotide is derived, or is substantially free of chemical precursors or other chemicals when chemically synthesized. The language "substantially free of cellular material" includes preparations of a nucleotide/oligonucleotide in which the nucleotide/oligonucleotide is separated from cellular components of the cells from which it is isolated or produced. Thus, a nucleotide/oligonucleotide that is substantially free of cellular material includes preparations of the nucleotide having less than about 30%, 20%, 10%, 5%, 2.5%, or 1%, (by dry weight) of contaminating material. When nucleotide/oligonucleotide is produced by chemical synthesis, it is preferably substantially free of chemical precursors or other chemicals, i.e., it is separated from chemical precursors or other chemicals which are involved in the synthesis of the protein. Accordingly, such preparations of the nucleotide/oligonucleotide have less than about 30%, 20%, 10%, or 5% (by dry weight) of chemical precursors or compounds other than the nucleotide/oligonucleotide of interest. In a preferred embodiment of the present invention, the nucleotide/oligonucleotide is isolated or purified.

As used herein, the term "isolated" bacteria is one which is separated from other organisms which are present in the natural source of the bacteria, e.g., biological material such as cells, blood, serum, plasma, saliva, urine, stool, sputum, nasopharyngeal aspirates, and so forth. The isolated bacteria can optionally be used to infect a subject cell.

As used herein, the term "biological sample" is defined as sample obtained from a biological organism, a tissue, cell, cell culture medium, or any medium suitable for mimicking biological conditions, or from the environment. Non-limiting examples include saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions, throat or nasal materials. In a preferred embodiment, bacterial agents are contained in serum, whole blood, nasopharyngeal fluid, throat fluid, or other respiratory fluid.

As used herein, the term "medium" refers to any liquid or fluid biological sample in the presence or absence of bacteria. Non-limiting examples include buffered saline solution, cell culture medium, acetonitrile, trifluoroacetic acid, combinations thereof, or any other fluid recognized in the art as suitable for combination with bacteria or other cells, or for dilution of a biological sample or amplification product for analysis.

To determine the percent identity of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, *PNAS* 87:2264 2268, modified as in Karlin and Altschul, 1993, *PNAS*. 90:5873 5877. Such an algorithm is incorporated into the NBLAST and XBLAST programs of Altschul et al., 1990, *J. Mol. Biol.* 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, *Nucleic Acids Res.* 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

As used herein, the terms "subject" and "patient" are synonymous and refer to a human or non-human animal, preferably a mammal including a human, non-primate such as cows, pigs, horses, goats, sheep, cats, dogs, avian species and rodents; and a non-human primate such as monkeys, chimpanzees, and apes; and a human, also denoted specifically as a "human subject".

The instant inventive process provides a rapid, specific, and sensitive assay process for detection of *Bordetella* spp. in biological samples by amplifying one or more nucleotide sequences that allow an investigator to distinguish between species and are present in a biological sample by processes similar to the polymerase chain reaction (PCR). The invention is preferably used to distinguish *B. pertussis, B. parapertussis*, and *B. holmesii*.

A family of forward and reverse nucleotide primer pairs is provided that each amplify a portion of one or more species of *Bordetella*. In the inventive process an oligonucleotide forward primer with a nucleotide sequence complementary to a unique sequence in a *Bordetella* nucleotide sequence, illustratively in the IS481 sequence (GenBank Accession No. M28220), is hybridized to its complementary sequence and extended. Similarly, a reverse oligonucleotide primer complementary to a second strand of *Bordetella* DNA in the same or an alternate region is hybridized and extended. This system allows for amplification of specific nucleotide sequences and is operable for simultaneous or sequential detection systems.

The present invention relates to the use of sequence information of *Bordetella* for diagnostic processes. More particularly, the present invention provides a process for detecting the presence or absence of nucleic acid molecules of one or more *Bordetella* species, natural or artificial variants, analogs, or derivatives thereof, in a biological sample. The process involves obtaining a biological sample from one or more various sources and contacting the sample with a compound or an agent capable of detecting a nucleic acid sequence of *Bordetella* spp., natural or artificial variants, analogs, or derivatives thereof, such that the presence of *Bordetella*, natural or artificial variants, analogs, or derivatives thereof, is detected in the sample. In a preferred embodiment, the presence of *B. pertussis, B. holmesii*, or *B. parapertussis*, natural or artificial variants, analogs, or derivatives thereof, is detected in the sample by a real-time polymerase chain reaction (real-time PCR) using primers that are constructed based on a partial nucleotide sequence of the *B. pertussis* genome.

Preferably, detection of one or more species of *Bordetella* is accomplished by amplification of particular nucleotide sequences specific for one of *B. pertussis, B. holmesii*, or *B. parapertussis*. More preferably, a region specific to *B. pertussis* and *B. holmesii* is the IS481 sequence which encompasses nucleotides 862-927 of GenBank Accession No. M28220. A nucleotide sequence specific for *B. holmesii* is hIS1001 sequence which encompasses nucleotides 41-107 of GenBank Accession No. AY786982. A nucleotide sequence specific for *B. parapertussis* is pIS1001 sequence which encompasses nucleotides 135-199 of GenBank Accession No. X66858. A nucleotide sequence specific for *B. parapertussis* and *B. pertussis* but is not detectable in *B. holmesii* is ptxS1 sequence which encompasses the sequence of GenBank Accession No. M14378.

In a preferred embodiment, a forward primer to be used in a real-time PCR process is 5'-CAAGGCCGAACGCTTCAT-3' (SEQ ID NO: 1), and a reverse primer 5'-GAGTTCTGG-TAGGTGTGAGCGTAA-3' (SEQ ID NO: 2). Illustratively, the forward primer and reverse primer are used to amplify a region of *Bordetella* nucleotide sequence to produce a first amplification product.

A preferred agent for detecting *Bordetella* spp. nucleic acid sequences, or a first amplification product produced therefrom, is a labeled nucleic acid probe capable of hybridizing thereto or to amplification products produced by PCR amplification of a region between a forward and reverse primer pair. In the above preferred embodiment, the nucleic acid probe is a nucleic acid molecule comprising or consisting of the nucleic acid sequence of 5'-CAGTCGGCCTTGCGT-GAGTGGG-3' (SEQ ID NO: 3), which sufficiently specifically hybridizes under stringent conditions to a *B. pertussis* nucleic acid sequence.

Preferably, the inventive process is operable to distinguish or detect one or more species of *Bordetella*. Illustratively, the inventive process is operable to detect one or more of *B. pertussis*, *B. parapertussis*, and *B. holmesii* and identify whether one or more of these or other *Bordetella* strains are present in a biological sample.

8). The amplification product of this region of the IS1001 sequence is specific to *B. parapertussis*. This amplification product is preferably detected by a non-degenerate probe. Preferably the non-degenerate probe is 5'-AGAC-CCAGGGCGCACGCTGTC-3' (SEQ ID NO: 9).

Primer and probe sequences most preferred in the subject invention are illustrated in Table 1.

TABLE 1

Sequences of primers and probes

| Target | Primer/Probe | Sequence 5'→3' | Amplicon Length (bp) |
|---|---|---|---|
| IS481[a] | 825U18 | CAAGGCCGAACGCTTCAT (SEQ ID NO: 1) | 66 bp |
| | 894L24 | GAGTTCTGGTAGGTGTGAGCGTAA (SEQ ID NO: 2) | |
| | 871U22P[b] | CAGTCGGCCTTGCGTGAGTGGG (SEQ ID NO: 3) | |
| hIS1001[c] | BHIS41U20 | GGCGACAGCGAGACAGAATC (SEQ ID NO: 4) | 67 bp |
| | BHIS91L17 | GCCGCCTTGGCTCACTT (SEQ ID NO: 5) | |
| | BHIS62U28P[d] | CGTGCAGATAGGCTTTTAGCTTGAGCGC ((SEQ ID NO: 6) | |
| pIS1001[e] | 135U17 | TCGAACGCGTGGAATGG (SEQ ID NO: 7) | 65 bp |
| | 199L20 | GGCCGTTGGCTTCAAATAGA (SEQ ID NO: 8) | |
| | 157U21PHEX[f] | AGACCCAGGGCGCACGCTGTC (SEQ ID NO: 9) | |
| ptxS1[g] | 402U16 | CGCCAGCTCGTACTTC (SEQ ID NO: 10) | 55 bp |
| | 422L15 | GATACGGCCGGCATT (SEQ ID NO: 11) | |
| | 419U22P[b] | AATACGTCGACACTTATGGCGA (SEQ ID NO: 12) | |

[a] Accession no. M28220.
[b] Probe 5' end labeled with 6-carboxyfluorescein FAM™ and 3' end labeled with Black Hole Quencher® 1 (BHQ1).
[c] Accession no. AY786982.
[d] Probe 5' end labeled with Quasar 670 and 3' end labeled with Black Hole Quencher® 2 (BHQ2).
[e] Accession no. X66858.
[f] Probe 5' end labeled with HEX™ and 3' end labeled with Black Hole Quencher® 1 (BHQ1).
[g] Accession no. M14378

*B. holmesii* is illustratively detected using a forward primer of 5'-GGCGACAGCGAGACAGAATC-3' (SEQ ID NO: 4) and reverse primer of 5'-GCCGCCTTGGCTCACTT-3' (SEQ ID NO: 5). Surprisingly, this primer pair will amplify the hIS1001 region of *B. holmesii* and is specific for this strain demonstrating no amplification of *B. pertussis* or *B. parapertussis*. The IS1001 insertion sequence is a 1,306 bp sequence containing inverted repeats at its termini. (van der Dee, A, et al., *J. Bacteriol.*, 1993; 75:141-147.) IS1001 was identified as an insertion element in *B. parapertussis* and has been used to detect the presence of *B. parapertussis* in biological samples to distinguish *B. parapertussis* from *B. pertussis*. Id. The hIS1001 sequence encompasses the sequence of GenBank Accession No. AY786982. The region amplified by primers SEQ ID NOS: 4 and 5 reveals that this insertion is present in *B. holmesii* and the sequence amplified is specific only to *B. holmesii*.

Detection of the preferred amplification product of SEQ ID NOS: 4 and 5 is accomplished by hybridizing a non-degenerate probe complementary to the amplification product. Illustratively, a probe operable is 5'-CGTGCAGATAG-GCTTTTAGCTTGAGCGC-3'(SEQ ID NO: 6). It is appreciated that all probes used herein are optionally modified, or replaced by a different sequence capable to detecting an amplification product within the target amplification product sequence.

A third species of *Bordetella*, *B. parapertussis*, is optionally detected or distinguished in the inventive process. The insertion element pIS1001 (GenBank Accession No. X66858) is preferably amplified by forward primer 5'-TC-GAACGCGTGGAATGG-3' (SEQ ID NO: 7) and reverse primer 5'-GGCCGTTGGCTTCAAATAGA-3' (SEQ ID NO:

The IS481 assay targets a region downstream from the inverted repeat generating a 66-bp amplicon, and the ptxS1 assay targets a region approximately 400 bp downstream of the start codon of the pertussis toxin subunit 1, the ptxA gene, generating a 55-bp amplicon.

The process of the present invention can involve a real-time quantitative PCR assay. In a preferred embodiment, the quantitative PCR used in the present invention is TaqMan assay (Holland et al., *PNAS* 88(16):7276 (1991)). It is appreciated that the current invention is amenable to performance on other real-time PCR systems and protocols that use alternative reagents illustratively including, but not limited to Molecular Beacons probes, Scorpion probes, multiple reporters for multiplex PCR, combinations thereof, or other DNA detection systems.

The assays are performed on an instrument designed to perform such assays, for example those available from Applied Biosystems (Foster City, Calif.). In more preferred specific embodiments, the present invention provides a real-time quantitative PCR assay to detect the presence of one or more *Bordetella* species, natural or artificial variants, analogs, or derivatives thereof, in a biological sample by subjecting the *Bordetella* nucleic acid from the sample to PCR reactions using specific primers, and detecting the amplified product using a probe. In preferred embodiments, the probe is a TaqMan® probe which consists of an oligonucleotide with a 5'-reporter dye and a 3'-quencher dye.

A fluorescent reporter dye, such as FAM™ dye (illustratively 6-carboxyfluorescein), is covalently linked to the 5' end of the oligonucleotide probe. Other dyes illustratively include TAMRA™, AlexaFluor™ dyes such as AlexaFluor™ 495 or 590, Cascade Blue®, Marine Blue®, Pacific Blue®, Oregon Green®, Rhodamine, Fluoroscein, TET™, HEX™, Cy5™, Cy3™, Quasar670, and Tetramethylrhodamine. Each of the reporters is quenched by a dye at the 3' end or other non-fluorescent quencher. Quenching molecules are suitably matched to the fluorescence maximum of the dye. Any suitable fluorescent probe for use in real-time PCR detection systems is illustratively operable in the instant invention. Similarly, any quenching molecule for use in real-time PCR systems is illustratively operable. In a preferred embodiment a 6-carboxyfluorescein reporter dye is present at the 5'-end and matched to BLACK HOLE QUENCHER® (BHQ1, Biosearch Technologies, Inc., Novato, Calif.). The fluorescence signals from these reactions are captured at the end of extension steps as PCR product is generated over a range of the thermal cycles, thereby allowing the quantitative determination of the bacterial load in the sample based on an amplification plot.

The Bordetella nucleic acid sequences are optionally amplified before being detected. The term "amplified" defines the process of making multiple copies of the nucleic acid from a single or lower copy number of nucleic acid sequence molecule. The amplification of nucleic acid sequences is carried out in vitro by biochemical processes known to those of skill in the art. The amplification agent may be any compound or system that will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, AmpliTaq Gold DNA Polymerase from Applied Biosystems, other available DNA polymerases, reverse transcriptase (preferably iScript RNase H+ reverse transcriptase), ligase, and other enzymes, including heat-stable enzymes (i.e., those enzymes that perform primer extension after being subjected to temperatures sufficiently elevated to cause denaturation). In a preferred embodiment, the enzyme is hot-start iTaq DNA polymerase from Bio-rad (Hercules, Calif.). Suitable enzymes will facilitate combination of the nucleotides in the proper manner to form the primer extension products that are complementary to each mutant nucleotide strand. Generally, the synthesis is initiated at the 3'-end of each primer and proceed in the 5'-direction along the template strand, until synthesis terminates, producing molecules of different lengths. There may be amplification agents, however, that initiate synthesis at the 5'-end and proceed in the other direction, using the same process as described above. In any event, the process of the invention is not to be limited to the embodiments of amplification described herein.

One process of in vitro amplification, which is used according to this invention, is the polymerase chain reaction (PCR) described in U.S. Pat. Nos. 4,683,202 and 4,683,195. The term "polymerase chain reaction" refers to a process for amplifying a DNA base sequence using a heat-stable DNA polymerase and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation produce rapid and highly specific amplification of the desired sequence. Many polymerase chain processes are known to those of skill in the art and may be used in the process of the invention. For example, DNA is subjected to 30 to 35 cycles of amplification in a thermocycler as follows: 95° C. for 30 sec, 52 to 60° C. for 1 min, and 72° C. for 1 min, with a final extension step of 72° C. for 5 min. For another example, DNA is subjected to 35 polymerase chain reaction cycles in a thermocycler at a denaturing temperature of 95° C. for 30 sec, followed by varying annealing temperatures ranging from 54 to 58° C. for 1 min, an extension step at 70° C. for 1 min, with a final extension step at 70° C. for 5 min. The parameters of PCR cycling times and number of steps are dependent on the primer pair, their melting temperature, and other considerations obvious to those known in the art. It is appreciated that optimizing PCR parameters for various probe sets is well within the skill of the art and is performed as mere routine optimization.

The primers for use in amplifying the nucleic acid sequences of *Bordetella* may be prepared using any suitable process, such as conventional phosphotriester and phosphodiester processes or automated embodiments thereof so long as the primers are capable of hybridizing to the nucleic acid sequences of interest. One process for synthesizing oligonucleotides on a modified solid support is described in U.S. Pat. No. 4,458,066. The exact length of primer will depend on many factors, including temperature, buffer, and nucleotide composition. The primer generally must prime the synthesis of extension products in the presence of the inducing agent for amplification.

Primers used according to the process of the invention are complementary to each strand of nucleotide sequence to be amplified. The term "complementary" means that the primers must hybridize with their respective strands under conditions, which allow the agent for polymerization to function. In other words, the primers that are complementary to the flanking sequences hybridize with the flanking sequences and permit amplification of the nucleotide sequence. Preferably, the 3' terminus of the primer that is extended is perfectly base paired with the complementary flanking strand. Preferably, probes possess nucleotide sequences complementary to one or more strands of the amplification product such as from IS481, hIS1001, or pIS1001. More preferably, the primers are complementary to genetic sequences of *B. pertussis* IS481 insert as illustrated in Accession No. M28220; *B. holmesii* as illustrated in Accession No. AY786982; and for *B. parapertussis* as illustrated in Accession No. X66858. Most preferably, primers contain the nucleotide sequences of SEQ ID NOS: 1 and 2; 4 and 5; and 7 and 8. It is appreciated that the complement of the aforementioned primer and probe sequences are similarly suitable for use in the instant invention. It is further appreciated that oligonucleotide sequences that hybridize with the inventive primer and probes are also similarly suitable. Finally, multiple positions are available for hybridization on the *Bordetella* genome and will be also suitable hybridization with a probe when used with the proper forward and reverse primers.

Those of ordinary skill in the art will know of various amplification processes that can also be utilized to increase the copy number of target nucleic acid sequence. The nucleic acid sequences detected in the process of the invention are optionally further evaluated, detected, cloned, sequenced, and the like, either in solution or after binding to a solid support, by any process usually applied to the detection of a specific nucleic acid sequence such as another polymerase chain reaction, oligomer restriction (Saiki et al., *BioTechnology* 3:1008 1012 (1985)), allele-specific oligonucleotide (ASO) probe analysis (Conner et al., *PNAS* 80: 278 (1983)), oligonucleotide ligation assays (OLAs) (Landegren et al., *Science* 241:1077 (1988)), RNase Protection Assay and the like. Molecular techniques for DNA analysis have been reviewed (Landegren et al., *Science* 242:229 237 (1988)). Following DNA amplification, the reaction product may be detected by Southern blot analysis, with or without using radioactive probes. In such a process, for example, a small sample of DNA containing the nucleic acid sequence obtained from the tissue or subject is amplified, and analyzed via a Southern blotting technique. The use of non-radioactive probes or labels is facilitated by the high level of the amplified signal. In one embodiment of the invention, one nucleoside triphosphate is radioactively labeled, thereby allowing direct visualization of the amplification product by autoradiography. In another embodiment, amplification primers are fluorescently labeled and run through an electrophoresis system. Visualization of amplified products is by laser detection followed by computer assisted graphic display, without a radioactive signal.

Other methods of detecting amplified oligonucleotide illustratively include gel electrophoresis, mass spectrometry, liquid chromatography, fluorescence, luminescence, gel mobility shift assay, fluorescence resonance energy transfer, nucleotide sequencing, enzyme-linked immunoadsorbent assay, affinity chromatography, chromatography, immunoenzymatic methods (Ortiz, A and Ritter, E, *Nucleic Acids Res.,* 1996; 24:3280-3281), streptavidin-conjugated enzymes, DNA branch migration (Lishanski, A, et al., *Nucleic Acids Res.,* 2000; 28(9):e42), enzyme digestion (U.S. Pat. No. 5,580,730), colorimetric methods (Lee, K, *Biotechnology Letters,* 2003; 25:1739-1742), or combinations thereof.

The term "labeled" with regard to the probe is intended to encompass direct labeling of the probe by coupling (i.e., physically linking) a detectable substance to the probe, as well as indirect labeling of the probe by reactivity with another reagent that is directly labeled. Examples of indirect labeling include detection of a probe using a fluorescently labeled antibody and end-labeling or centrally labeling of a DNA probe with biotin such that it can be detected with fluorescently labeled streptavidin. The detection method of the invention can be used to detect RNA (particularly mRNA) or genomic nucleic acid in a sample in vitro as well as in vivo. For example, in vitro techniques for detection of nucleic acid include northern hybridizations, in situ hybridizations, RT-PCR, real-time PCR, and DNase protection. Furthermore, in vivo techniques for detection of *Bordetella* include introducing into a subject organism a labeled antibody directed against a membrane or other polypeptide component or directed against a particular nucleic acid sequence of *Bordetella*. For example, the antibody can be labeled with a radioactive marker whose presence and location in the subject organism can be detected by standard imaging techniques, including autoradiography.

The size of the primers used to amplify a portion of the nucleic acid sequence of *Bordetella* is at optionally least 5, and often 10, 15, 20, 25, or 30 nucleotides in length. Preferably, the GC ratio should be above 30%, 35%, 40%, 45%, 50%, 55%, or 60% so as to prevent hair-pin structure on the primer. Furthermore, the amplicon should be sufficiently long enough to be detected by standard molecular biology methodologies. The forward primer is preferably shorter than the reverse primer. Techniques for modifying the $T_m$ of either primer are operable herein. An illustrative forward or reverse primer contains LNA-dA and LNA-dT (Glen Research Corporation) so as to match $T_m$ with a corresponding alternate primer.

An inventive process uses a polymerization reaction which employs a nucleic acid polymerizing enzyme, illustratively a DNA polymerase, RNA polymerase, reverse transcriptase, or mixtures thereof. It is further appreciated that accessory proteins or molecules are present to form the replication machinery. In a preferred embodiment the polymerizing enzyme is a thermostable polymerase or thermodegradable polymerase. Use of thermostable polymerases is well known in the art such as Taq polymerase available from Invitrogen Corporation. Thermostable polymerases allow a polymerization reaction to be initiated or shut down by changing the temperature or other condition in the reaction mixture without destroying activity of the polymerase.

Accuracy of the base pairing in the preferred embodiment of DNA sequencing is provided by the specificity of the enzyme. Error rates for Taq polymerase tend to be false base incorporation of $10^{-5}$ or less. (Johnson, *Annual Reviews of Biochemistry,* 1993: 62:685-713; Kunkel, *Journal of Biological Chemistry,* 1992; 267:18251-18254). Specific examples of thermostable polymerases illustratively include those isolated from *Thermus aquaticus, Thermus thermophilus, Pyrococcus woesei, Pyrococcus furiosus, Thermococcus litoralis* and *Thermotoga maritima*. Thermodegradable polymerases illustratively include *E. coli* DNA polymerase, the Klenow fragment of *E. coli* DNA polymerase, T4 DNA polymerase, T7 DNA polymerase and other examples known in the art. It is recognized in the art that other polymerizing enzymes are similarly suitable illustratively including *E. coli*, T7, T3, SP6 RNA polymerases and AMV, M-MLV, and HIV reverse transcriptases.

The polymerases are optionally bound to the primer. When the genetic material of *Bordetella* is a single-stranded DNA molecule due to heat denaturing the polymerase is bound at the primed end of the single-stranded nucleic acid at an origin of replication. A binding site for a suitable polymerase is optionally created by an accessory protein or by any primed single-stranded nucleic acid.

In a further embodiment detection of PCR products is achieved by mass spectrometry. Mass spectrometry has several advantages over real-time PCR systems in that it can be used to simultaneously detect the presence of *Bordetella* and decipher mutations in target nucleic acid sequences allowing identification and monitoring of emerging strains. Further, mass spectrometers are prevalent in the clinical laboratory. Similar to fluorescence based detection systems mass spectrometry is capable of simultaneously detecting multiple amplification products for a multiplexed and controlled approach to accurately quantifying components of biological or environmental samples.

Multiple mass spectrometry platforms are suitable for use in the instant invention illustratively including matrix assisted laser desorption ionization time of flight mass spectrometry (MALDI), electrospray mass spectrometry, electrospray ionization-Fourier transform ion cyclotron resonance mass spectrometry (ESI-FTICR), multi-stage mass spectrometry fragmentation analysis (MS/MS), mass spectrometry coupled with liquid chromatography such as high performance liquid chromatography mass spectrometry (HPLC) and ultra performance liquid chromatography isotope dilution tandem mass spectrometry (HPLC-ID/MS/MS), and variations thereof.

It is appreciated that numerous other detection processes are similarly suitable for measuring an amplification product by detecting a detection signal. Illustrative examples include, but are not limited to, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time PCR, gel electrophoresis, or combinations thereof.

Preferably, PCR amplification products are generated using complementary forward and reverse oligonucleotide primers. In a non-limiting example, *Bordetella* genetic sequences or fragments thereof are amplified by the primer pair SEQ ID NOS: 1 and 2 that amplify a conserved sequence in the IS481 insertion sequence and is useful to detect *B.*

*pertussis* and/or *B. holmesii*. The resulting amplification product is processed and prepared for detection by processes known in the art. It is appreciated that the complements of SEQ ID NOS: 1 and 2 are similarly suitable for use in the instant invention. It is further appreciated that oligonucleotide sequences that hybridize with SEQ ID NO: 1 or 2 are also similarly suitable. Finally, multiple positions are available for hybridization on the *Bordetella* genome and will be also suitable hybridization with forward and reverse primers that may or may not be used with a probe for real-time PCR.

Optionally, multiple amplification products are simultaneously produced in a PCR reaction that is then available for simultaneous detection and quantification. Thus, multiple detection signals are inherently produced or emitted that are separately and uniquely detected in one or more detection systems. It is appreciated that multiple detection signals are optionally produced in parallel. Preferably, a single biological sample is subjected to analysis for the simultaneous or sequential detection of *Bordetella* genetic sequences. It is appreciated that three or more independent or overlapping sequences are simultaneously or sequentially measured in the instant inventive process. Oligonucleotide matched primers (illustratively SEQ ID NOS: 1 and 2) are simultaneously or sequentially added and the biological sample is subjected to proper thermocycling reaction parameters. For detection by mass spectrometry a single sample of the amplification products from each gene are simultaneously analyzed allowing for rapid and accurate determination of the presence of *Bordetella*. Optionally, analysis by real-time PCR is employed capitalizing on multiple probes with unique fluorescent signatures. Thus, each gene or other genetic sequence is detected without interference by other amplification products. This multi-target approach increases confidence in quantification and provides for additional internal control.

In a preferred embodiment a triplex approach is used for the simultaneous detection and distinguishing of three *Bordetella* species. Preferably, *B. pertussis*, *B. parapertussis*, and *B. holmesii* are each detectable in a single biological sample simultaneously. Each real-time PCR assay normally takes approximately 90-100 minutes to run on the instrument. Combining three assays into one reduces the run time in a preferred embodiment from 300 minutes to 100 minutes. Similarly, utilizing the multiplex assay is cost effective. Instead of using master mixes, plastics, etc. for three individual assays, only one assay is run such that the cost is approximately ⅓ that of three assays.

Illustratively, three sets of matched primer pairs are used. Preferably, SEQ ID NOS: 1 and 2 are operable for amplification of nucleotide sequences present in *B. pertussis* and possibly *B. holmesii*. SEQ ID NOS: 4 and 5 are operable for amplification of nucleotide sequences present in and specific for *B. holmesii*. SEQ ID NOS: 7 and 8 are for amplification of nucleotide sequences present in and specific for *B. parapertussis*. Thus, simultaneous presence of all three primer pairs in a single reaction chamber will produce first, second, and third amplification products in a biological sample containing all three species of *Bordetella*. If a biological sample contains only *B. pertussis*, only the first amplification product will be produced as no nucleotide sequences are present for SEQ ID NOS: 4 and 5 or 7 and 8 to hybridize to. Similarly, if a biological sample contains a co-infection with *B. pertussis* and *B. parapertussis*, a first and a third amplification product will be produced and a second amplification product (illustratively specific to *B. holmesii*) will be absent. Thus, the presence of the first and third amplification products will signal a co-infection with *B. pertussis* and *B. parapertussis*.

It is appreciated that the IS481 sequence amplified when primers SEQ ID NO: 1 and SEQ ID NO: 2 are used will produce an amplification product with either a *B. pertussis* or a *B. holmesii* infection. Thus, when a biological sample contains a co-infection of *B. pertussis* and *B. holmesii* a first amplification product will be produced. Similarly, in a biplex or triplex assay where primers SEQ ID NOS: 4 and 5 are used in addition to SEQ ID NOS: 1 and 2, two amplification products will be observed indicating the presence of a co-infection of B. holmesii and *B. pertussis* or possibly a single infection of *B. holmesii*.

However, to date no reports of a co-infection of *B. pertussis* and *B. holmesii* in a human population has been reported or observed in studies of a large number of biological samples from patients suspected of having a *Bordetella* infection. It is not expected that this cross-reactivity will be detrimental to clinical analysis, particularly when the inventive triplex assay is employed in conjunction with the inventive ptxS1 assay describe ante.

The ptxS1 assay capitalizes on the unconventional search for a nucleotide sequence that will detect multiple *Bordetella* species. (See Tatti, K M, et al., *Diag. Micro. Infec. Dis.*, 2008; 61:264-271 the contents of which are fully incorporated herein by reference, particularly for description of ptxS1 and IS481 amplifications.) Specifically, the inventor sought to locate a nucleotide sequence that is specific for both *B. pertussis* and *B. parapertussis*, but is absent from *B. holmesii*. Primers 5'-CGCCAGCTCGTACTTC-3' (SEQ ID NO: 10) and 5'-GATACGGCCGGCATT-3' (SEQ ID NO: 11) are employed to amplify a sequence that will not produce a reaction product indicative of *B. holmesii*. Thus, in the above triplex inventive assay should (first) primers SEQ ID NOS: 1 and 2 and (second) primers SEQ ID NOS: 4 and 5 each produce a first and second amplification product, a parallel or subsequent analysis by the ptxS1 analysis will identify whether there is a dual infection of *B. pertussis* and *B. holmesii* or a single infection of *B. holmesii*. A positive ptxS1 assay will indicate a co-infection whereas a negative ptxS1 assay will indicate a single infection with *B. holmesii*.

The inventive ptxS1 assay is similarly operable in a real-time PCR assay. A probe sequence that recognizes the amplification product of the ptxS1 nucleic acid sequence is operable to detect increasing copy number of the amplification product. Preferably, a probe sequence is 5'-AATACGTCGACACTTATGGCGA-3' (SEQ ID NO: 12).

Optionally, a quadraplex assay is performed where four matched primer sets are simultaneously used to analyze a biological sample for IS481, hIS1001, pIS1001, and ptxS1. This assay system is operable without the need for a second confirmatory ptxS1 assay. However, as clinical laboratories are continually seeking the least cost solution and since no co-infection of *B. holmesii* and *B. pertussis* has been observed and reported, the need for quadraplex assay will be user specific.

In a specific embodiment, the processes further involve obtaining a control sample from a control subject, contacting the control sample with a compound or agent capable of detecting the presence of *Bordetella* nucleic acid in the sample, and comparing the presence of mRNA or genomic DNA in the control sample with the presence of mRNA or genomic DNA in the test sample.

The invention also encompasses kits for detecting the presence of *Bordetella* nucleic acid sequences in a test sample. The kit, for example, includes a labeled compound or agent capable of detecting a nucleic acid molecule in a test sample and, in certain embodiments, for determining the titer in the sample.

For oligonucleotide-based kits, the kit includes, for example: (1) an oligonucleotide, e.g., a detectably labeled oligonucleotide, that hybridizes to a nucleic acid sequence of the *Bordetella* species of interest and/or (2) a pair of primers (one forward and one reverse) useful for amplifying a nucleic acid molecule containing the *Bordetella* sequence. The kit can also comprise ancillary agents, e.g., a buffering agent, a preservative, or a protein stabilizing agent. The kit can also comprise components necessary for detecting the detectable agent (e.g., an enzyme or a substrate). The kit can also contain a control sample or a series of control samples which is assayed and compared to the test sample contained. Each component of the kit is usually enclosed within an individual container and all of the various containers are usually enclosed within a single package along with instructions for use.

The instant inventive processes are amenable to use for diagnosis of *Bordetella* infection in a subject, insects, and any inclusive other organism capable of infection or transfection by or with *Bordetella*.

To increase confidence and to serve as an internal or external control, a purified and titered *Bordetella* solution is used as a biological sample. It is appreciated that any target *Bordetella* species is operable as a control. Illustratively, a control sample includes *B. pertussis, B. holmesii, B. parapertussis*, or combinations thereof. By amplification of a single sample with known quantities of *Bordetella* or of a set of samples representing a titration of *Bordetella*, the level of *Bordetella* in the unknown biological sample is determined. Preferably, the purified and titered *Bordetella* solution is analyzed in parallel with the unknown biological sample to reduce inter assay error or to serve as a standard curve for quantitation of unknown *Bordetella* in the biological sample. Using purified and titered *Bordetella* solution provides for a similar complete genetic base DNA strand for amplification.

In another embodiment, a subgenomic fragment is cloned into a plasmid for amplification, purification, and use as a quantitative comparator or nucleic acid calibrator. In a non-limiting example, a DNA subgenomic fragment of *B. pertussis* is optionally amplified from a positive nasal swab using primers bracketing the PCR target regions in the IS481 sequence. It is appreciated that other sequences are similarly suitable for use as a quantitative control. The known concentration of the subgenomic fragment is used to create a standard curve for quantitative determinations and to access amplification efficiency.

Also provided is a kit for detecting *Bordetella* infection that contains reagents for the amplification, or direct detection of *Bordetella* or portions thereof. An exemplary kit illustratively includes a forward and reverse primer pair, a non-degenerate probe. In a preferred embodiment, the forward and reverse primers have the oligonucleotide sequence SEQ ID NOS: 1 and 2 and a nondegenerate probe of the sequence SEQ ID NO: 3. It is appreciated that a diagnostic kit may optionally contain primers and probes that are the complements of SEQ ID NOS 1-3 or that hybridize with oligonucleotides SEQ ID NOS: 1-3. It is further appreciated that a diagnostic kit optionally includes ancillary reagents such as buffers, solvents, thermostable polymerases, nucleotides, and other reagents necessary and recognized in the art for amplification and detection of *Bordetella* in a biological sample.

In a preferred embodiment a kit includes reagents for detection and distinguishing three or more species of *Bordetella*. Preferably, a kit includes reagents for detection and distinguishing *B. pertussis, B. holmesii*, and *B. parapertussis*.

Most preferably, a kit includes primers and probes of SEQ ID NOS: 1-9. Optionally, a kit may also include reagents of SEQ ID NOS: 10-12.

The invention provides a host cell containing a nucleic acid sequences according to the invention as an alternative to synthetic primer sequence generation. Plasmids containing the polymerase components of the *Bordetella* bacteria are generated in prokaryotic cells for the expression of the components in relevant cell types (bacteria, insect cells, eukaryotic cells). Preferably, the cell line is a primate cell line. These cell lines may be cultured and maintained using known cell culture techniques such as described in Celis, Julio, ed., 1994, Cell Biology Laboratory Handbook, Academic Press, NY. Various culturing conditions for these cells, including media formulations with regard to specific nutrients, oxygen, tension, carbon dioxide and reduced serum levels, can be selected and optimized by one of skill in the art.

The preferred cell line of the present invention is a prokaryotic cell line such as *E. coli* and the like for transiently or stably expressing one or more full-length or partial *Bordetella* proteins. Such cells can be made by transfection (proteins or nucleic acid vectors), infection (viral vectors) or transduction (viral vectors). The cell lines for use in the present invention are cloned using known cell culture techniques familiar to one skilled in the art. The cells are cultured and expanded from a single cell using commercially available culture media under known conditions suitable for propagating cells.

A host cell is a cell derived from a mammal, insect, yeast, bacteria, or any other single or multicellular organism recognized in the art. Host cells are optionally primary cells or immortalized derivative cells. Immortalized cells are those which can be maintained in vitro for several replication passages.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, NY, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, NY, 1991; and Methods of Immunological Analysis, ed. Masseyeff et al., John Wiley & Sons, NY, 1992. Additionally, numerous techniques and reagents operable herein are described in Tatti, K M, et al., *Diag. Micro. Infec. Dis.*, 2008; 61:264-271.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to mammalian cells, tissue, fluids, or subjects, a person having ordinary skill in the art recognizes that similar techniques and other techniques know in the art readily translate the examples to other mammals such as humans. Reagents illustrated herein are commonly cross reactive between mammalian species or alternative reagents with similar properties are commercially available, and a person of ordinary skill in the art readily understands where such reagents may be obtained.

EXAMPLE 1

Obtaining Bacterial Strains and Clinical Specimens

Bacterial strains are obtained from the CDC culture collections in the Meningitis and Vaccine Preventable Diseases Branch/Pertussis and Diphtheria Laboratory and other collaborators at CDC. Two hundred fifty-eight *Bordetella* spp. isolates are grown for 4 days at 37° C. under high humidity on modified Regan-Lowe medium containing charcoal agar (Oxoid, Basingstoke, UK) and 10% defibrinated horse blood. Other isolates were cultured following standard procedures.

A total of 101 clinical human specimens of nasopharyngeal aspirates or swabs were submitted to CDC during various cough-illness outbreaks (CDC, 2004, 2006, 2007). The specimens were cultured for *Bordetella* spp. upon arrival as described by Hardwick et al., 2002. In accordance with CDC human subjects guidelines, this study is considered exempt of institutional review board approval because the linkage to personally identifiable information is not accessible to CDC investigators.

EXAMPLE 2

Preparation of Nucleic Acid and Sequencing of Bacterial Strains

DNA extraction from clinical specimens or isolates is performed either on MagNA Pure LC equipment using MagNA Pure LC DNA Isolation Kit III (Roche Applied Science, Indianapolis, Ind.) or using the QIAampDNA Mini Kit (QIAGEN, Valencia, Calif.) following the manufacturers' instructions and eluted in 100 μL of either 10 mmol/L Tris-HCl buffer (pH 8.0) or water. DNA is extracted from clinical specimens obtained when the outbreaks occurred. Concentration of DNA extracted from isolates is determined with a NanoDrop® ND-1000 spectrophotometer (NanoDrop Technologies, Wilmington, Del.).

EXAMPLE 3

Preparation of Primers and Probes

The primers and probes are designed based on the nucleotide sequences of *B. pertussis* IS481 (GenBank Accession No. M28220), *B. holmesii* (GenBank Accession No. AY786982), *B. parapertussis* (GenBank Accession No. X66858), and ptxS1 (GenBank Accession No. M14378) using Primer Express 2.0 or 3.0 (Applied Biosystems, Foster City, Calif.), and analyzed using Oligo 6.0 (Molecular Biology Insights, Cascade, Colo.). Primers and probes are synthesized in the Biotechnology Core Facility at CDC using per solid support techniques known in the art (Table 1).

EXAMPLE 4

Real-time PCR to Identify and Distinguish *Bordetella* Species

Real-time PCR assays are performed on either a LightCycler or AB7500 instrument. Real-time PCR with the AB7500 instrument (Applied Biosystems) is performed in a total volume of 25 μL in an optical 96-well plate (Applied Biosystems). The amplification mixture contains 4 μL of extracted DNA plus a 21-μL TaqMan® Gene Expression PCR Master Mix (Applied Biosystems) with 100 nmol/L of each primer and 300 nmol/L of probe for IS481 target, 100 nmol/L of each primer and 100 nmol/L of probe for hIS1001 target, and 300 nmol/L of each primer and 100 nmol/L of probe for pIS1001 target. A similar assay mix is used for the ptxS1 target that contains 700 nmol/L of each primer and 300 nmol/L probe. The PCR protocol used is as follows: hold for 2 min at 50° C.; enzyme activation for 10 min at 95° C.; amplification for 15 s at 95° C. and 1 min at 60° C., repeat for 45 cycles. The PCR protocol for the ptxS1 assay was the same as for the triplex assay, except the annealing temperature is 57° C. Positive samples (strain A639) and nontemplate control samples (PCR grade water) are tested in triplicate in each run.

EXAMPLE 5

Assay Sensitivity

Assay sensitivity is determined by comparison of serial dilutions of representative *Bordetella* strains. A singleplex assay for each individual real-time PCR target consisting of a 10-fold serial dilution is run simultaneously with the multiplex assay for a comparison of cycle threshold (Ct) values. Sensitivity is measured using serially diluted *B. pertussis, B. parapertussis*, and *B. holmesii* isolates. Bacterial cultures are suspended in 10 mmol/L tris-buffered saline (TBS) (pH 7.2) at a concentration equivalent to $10^7$ cells/mL based on McFarland turbidometric standards. Serial 10-fold dilutions ($10^7$ to $10^0$ CFU/mL) are made from the suspension in TBS. Aliquots from each series of dilutions are used to spread plates in triplicate, and the average colony-forming unit per milliliter is calculated. DNA is extracted from the aliquots and tested in the real-time PCR assays in triplicate to determine the linear dynamic range and lower limit of detection (LLOD). A model of nonlinear regression (Sigma Plot version 9.0) is used for the dynamic range analysis, and the regression line represents data in the linear range. The PCR efficiency (E) of the primer pair and probe is calculated using the equation $E=10^{-1}/slope^{-1}$ (Vaerman et al., 2004). An E of 1.0 indicates that the amplicon quantity is duplicated every cycle (FIG. 1).

A stock concentration of 25 ng/μL of DNA from *B. pertussis* strain A639 is determined based on the absorption at A260, and 10-fold serial dilutions are tested in triplicate in the real-time PCR assays to determine the lower limit of detection (LLOD) per PCR reaction based on genome equivalents for both the LightCycler and AB7500 assays.

Each individual target assay achieves >99% efficiency with linear amplification over a 5-log dynamic range. The PCR efficiency (E) of each primer pair and probe set is near a value of 1 indicating that the amplicon quantity is duplicated every cycle and demonstrates an exponential amplification of DNA with each of the primer and probe sets. The IS481 assay achieves >99% efficiency with linear amplification over an 8-log dynamic range of $10^0$ to $10^7$ CFU/mL for *B. pertussis* (FIG. 1A), whereas the ptxS1 assay achieves >99% efficiency with linear amplification over a 6-log dynamic range of $10^2$ to $10^7$ CFU/mL for *B. pertussis* (FIG. 1B). The regression coefficients ($R^2$=0.996 and 0.997) and the amplification efficiencies (E=1.0105 and 1.009) for the IS481 and ptxS1 assays, respectively, demonstrated an exponential amplification of DNA with both primer and probe sets.

The multiplex assay demonstrates an amplification reaction pattern similar to a singleplex assay of each target (FIG. 2). The multiplex R-PCR assay increases the Ct values for each target slightly resulting in 1 genomic equivalent per reaction for *B. holmesii* IS/001-like (hIS1001) and IS481 but remains less than 1 genomic equivalent per reaction for the *B. pertussis IS*481 and the *B. parapertussis* pIS1001 targets (Table 2).

TABLE 2

Comparisons between single target real-time PCR assay
and multiplex real-time PCR assays.

B. pertussis DNA with FAM labeled IS481
Comparison between assays

| Genomic Equivalents | Singleplex Assay 300 nM/300 nM | Multiplex Assay 100 nM/300 nM |
|---|---|---|
| 10,000 | 16.76 | 17.22 |
| 1,000 | 19.43 | 20.06 |
| 100 | 23.02 | 23.50 |
| 10 | 26.35 | 27.39 |
| 1 | 30.77 | 30.55 |
| 0.1 | 33.52 | 34.21 |

B. holmesii DNA with FAM labeled IS481
Comparison between assays

| Genomic Equivalents | Singleplex Assay 100 nM/100 nM | Multiplex Assay 100 nM/100 nM |
|---|---|---|
| 10,000 | 21.54 | 22.21 |
| 1,000 | 25.66 | 26.19 |
| 100 | 29.36 | 30.10 |
| 10 | 33.75 | 34.08 |
| 1 | 37.06 | 37.53 |
| 0.1 | 42.21 | 40.00 |

B. holmesii DNA with IS1001 Quasar 670 labeled
Comparison between assays

| Genomic Equivalents | Singleplex Assay 100 nM/100 nM | Multiplex Assay 100 nM/100 nM |
|---|---|---|
| 10,000 | 22.12 | 22.62 |
| 1,000 | 25.69 | 26.13 |
| 100 | 29.38 | 29.80 |
| 10 | 33.74 | 34.01 |
| 1 | 38.11 | 37.61 |
| 0.1 | 41.07 | 40.82 |

B. parapertussis DNA with 5'Hex labeled IS1001
Comparison between assays

| Genomic Equivalents | Singleplex Assay 300 nM/100 nM | Multiplex Assay 300 nM/100 nM |
|---|---|---|
| 10,000 | 19.20 | 19.28 |
| 1,000 | 22.57 | 22.54 |
| 100 | 26.26 | 26.36 |
| 10 | 29.98 | 30.42 |
| 1 | 33.63 | 33.48 |
| 0.1 | 35.97 | 36.60 |

EXAMPLE 6

Specificity of Targets for B. Pertussis, B. Holmesii, and B. Parapertussis

Prior to the multiplex assay, a total of 258 *Bordetella* species isolates which includes 60 *B. pertussis*, 52 *B. parapertussis*, 70 *B. bronchiseptica*, and 72 *B. holmesii* are used in the individual evaluation of each real-time PCR target assay for cross-reactivity at a 5 ng/μl concentration. One isolate each of *B. avium*, *B. hinzii*, *B. petrii*, and *B. trematum* are also tested. All isolates are acquired from a human reservoir. The IS481 target sequence is completely specific for the *B. pertussis* and *B. holmesii* isolates. The hIS1001 target is specific to *B. holmesii*. The pIS1001 target is specific to *B. parapertussis* and shows no cross-reactivity with *B. pertussis* or *B. holmesii*, but reacts with 5 of 72 *B. bronchiseptica* isolates, however, *B. bronchiseptica* is expected to be of little clinical relevance to a human population.

A collection of non-*Bordetella* spp. (n=66) listed below (Table 3) and human DNA are also tested for cross-reactivity with each individual real-time PCR target. No cross-reactivity of the primer/probe sets is observed with DNA from these species.

TABLE 3

Specificity analyses

| Genus | Species | No. tested |
|---|---|---|
| Aerococcus | A. viridans | 1 |
| Bacillus | B. cereus, B. subtilis | 2 |
| Chlamydia | C. pneumoniae | 1 |
| Corynebacterium | C. diphtheriae, C. ulcerans, C. accolens, C. jeikeium, C.minutissimum, C. pseudodiphtheriticum,C. pseudotuberculosis, C. striatum | 8 |
| Enterococcus | E. faecalis | 1 |
| Escherichia | E. coli | 1 |
| Flavobacterium | F. meningosepticum | 1 |
| Gemella | G. haemolysans | 1 |
| Haemophilus | H. influenzae serotype, a, b, c, d, e, f, NT$^a$, H. haemolyticus, H. aegyptius, H. parainfluenzae | 10 |
| Legionella | L. pneumophila, L. longbeachae serogroup 1 and 2 | 3 |
| Moraxella | M. catarrhalis | 1 |
| Mycoplasma | M. pneumoniae | 1 |
| Neisseria | N. meningitidis serogroup, A, B, C, W135, X, Y, Z, 29E, NG$^b$, N. sicca, N. lactamica, N. subflava, N. cinerea | 13 |
| Pseudomonas | P. aeruginosa | 1 |
| Staphylococcus | S. aureus | 1 |
| Streptococcus | S. pneumoniae, S. agalactiae(2), S. pyogenes, S. canis, S .anginosus, S. equi, S. zooepidemicus, S. porcinus, S. dysgalactiae(2), S. constellatus, S. iniae, S. intermedius, S. bovis, S. pseudopneumoniae,S. mitis, S. oralis, S. sanguinis, S. salivarius | 20 |
| Total | | 66 |

EXAMPLE 7

Detection and Distinguishing Bordetella Species in Clinical Specimens

In the blinded retrospective study, 101 nasopharyngeal specimens collected in cough-illness outbreaks were tested using the multiplex and singleplex assays.

DNA extracted from nasopharyngeal specimens is assayed in triplicate with a water control placed between every 2 samples. An average cycle threshold (Ct) value of the multiplex PCR assays was calculated to give a final value. If a specimen is positive in 2 of 3 tests, it is considered positive. Clinical specimens are also tested for the human rnaseP gene using a real-time PCR assay to monitor the quality of DNA in the specimen and to check for inhibition as described by Tatti, K M, et al., *Diag. Micro. Infec. Dis.*, 2008; 61:264-271. To be considered positive for rnaseP, a specimen should have a Ct value<40. If a Ct value is greater than 40 or negative for rnaseP, a 1- to 5-fold dilution of the specimen in water is performed, and the multiplex assays are repeated on the diluted sample. The rnaseP results demonstrated amplifiable DNA without PCR inhibitors in all specimens. The range of Ct values for rnaseP was from 21.7 to 35.0.

A total of 24.7% of the clinical specimens were positive for *Bordetella* spp. by culture, whereas 30.7% were positive for *Bordetella* spp. by PCR supporting the accuracy of the inventive assay. Moreover, all 37 specimens that generated PCR amplicons gave comparable Ct values in both the singleplex and the multiplex assays. Of the 37 clinical specimens that generated Ct values, 6 specimens had 2 of 3 replicates with a high Ct value (Ct≥35) with IS481 alone and were interpreted as indeterminate. Sixty-four (63.4%) clinical specimens were culture and PCR negative.

Twenty-seven (26.7%) of the samples were positive for *B. pertussis* by real-time PCR demonstrating amplification of IS481, but no amplification of either hIS1001 or pIS1001.

Two clinical specimens were culture positive for *B. parapertussis* and PCR positive for both *B. pertussis* by IS481 and *B. parapertussis* by pIS1001. The results from the multiplex assay demonstrate that the specimens are in fact co-infections of the two species. This exemplifies the robustness of the multiplex assay.

Two samples were positive for *B. holmesii* by hIS1001 in the multiplex real-time PCR assay and negative by the ptxS1 assay which demonstrates infection only by B. holmesii and not *B. pertussis*. These results suggest that co-infection of *B. holmesii* and *B. pertussis* is extremely rare.

EXAMPLE 8

Detection of *Bordetella* Amplicons Via Mass Spectroscopy

Detection of amplification products obtained as in Example 4 was performed essentially as described by Blyn, L, et al. *J. Clin. Microbiol.* 2008; 46(2):644-651. Following amplification each PCR mixture is desalted and purified using a weak anion-exchange protocol based on the method of Jiang and Hofstadler (Jiang, Y, and S A Hofstadler. *Anal. Biochem.* 2003; 316:50-57). ESI-TOF is used to obtain accurate-mass (±1 ppm), high-resolution (M/ΔM, >10,000 full width half maximum) mass spectra. For each sample, approximately 1.5 µl of analyte solution is consumed during the spectral acquisition. Raw mass spectra are postcalibrated with an internal mass standard and deconvolved to average molecular masses. Quantitative results are obtained by comparing the peak heights with an internal PCR calibration standard present in every PCR well at 300 molecules unless otherwise indicated. This assay confirms the data obtained as in Example 7.

Patent applications and publications mentioned in the specification are indicative of the levels of those skilled in the art to which the invention pertains. The foregoing description is illustrative of particular embodiments of the invention, but is not meant to be a limitation upon the practice thereof. The following claims, including all equivalents thereof, are intended to define the scope of the invention.

The invention is hereby described with relation to the following references and those otherwise identified in the instant specification. Each reference is incorporated herein by reference as if each were laid out explicitly in its entirety in the instant specification including both text and figures. Each reference is incorporated for the individual point referred to in the specification as well as for all information contained therein and not explicitly identified in the specification. All references are representative of the knowledge of a person of skill in the art and illustrate other aspects of the present invention as envisioned by the inventors.

The invention claimed is:

1. A process of detecting and distinguishing *Bordetella pertussis, B. parapertussis*, and *B. holmesii* in a biological sample comprising:
   producing a first amplification product by amplifying a *Bordetella* nucleotide sequence if present in the sample using a forward primer consisting of the sequence of SEQ ID NO: 1 and a reverse primer consisting of the sequence of SEQ ID NO: 2, under conditions suitable for a polymerase chain reaction;

measuring said first amplification product;

producing a second amplification product by amplifying a *Bordetella* nucleotide sequence if present in the sample using a forward primer consisting of the sequence of SEQ ID NO: 4 and a reverse primer consisting of the sequence of SEQ ID NO: 5, under conditions suitable for a polymerase chain reaction, and measuring said second amplification product;

producing a third amplification product by amplifying a *Bordetella* nucleotide sequence if present in the sample using a forward primer consisting of the sequence of SEQ ID NO: 7 and a reverse primer consisting of the sequence of SEQ ID NO: 8, under conditions suitable for a polymerase chain reaction, and measuring said third amplification product;

said step of producing said first amplification product, said step of producing said second amplification product, and said step of producing said third amplification product performed in the same reaction chamber;

producing a fourth amplification product by amplifying a *Bordetella* nucleotide sequence using a forward primer consisting of the sequence of SEQ ID NO: 10 and a reverse primer consisting of the sequence of SEQ ID NO: 11, under conditions suitable for a polymerase chain reaction, and measuring said fourth amplification product;

detecting and distinguishing *Bordetella pertussis, B Bordetella parapertussis*, and *B Bordetella holmesii* in the sample based on a relative ratio of said first amplification product, said second amplification product, said third amplification product, and said fourth amplification product.

2. The process of claim 1 wherein measuring one or more of said first amplification product, said second amplification product, and said third amplification product uses as a probe consisting of the sequence of SEQ ID NO: 3 and a label and a quencher, SEQ ID NO: 6 and a label and a quencher, SEQ ID NO: 9 and a label and a quencher, or combinations of said probes as a detection probe, wherein one or more of said probes is hybridized to one or more of said amplification products; and detecting the presence or absence of a first detection signal, a second detection signal and/or a third detection signal from one or more of said probes.

3. The process of claim 1 further comprising providing a strain-specific *B. holmesii* negative probe consisting of the sequence of SEQ ID NO: 12 and a label and a quencher;

hybridizing said strain-specific probe under conditions suitable for a polymerase chain reaction to said complementary fourth amplification product to produce a fourth detection signal; and detecting the presence or absence of said detection signal from said probe of SEQ ID NO: 12.

4. The process of claim 3, wherein said first, second, third, or fourth detection signal is compared to a fifth detection signal from a nucleic acid calibrator extracted in parallel to said biological sample.

5. The process of claim 4, wherein said nucleic acid calibrator comprises a known amount of a *Bordetella* bacteria and a known amount of a medium.

6. The process of claim 4 wherein said fifth detection signal is generated by PCR amplification of a titered *Bordetella* solution.

7. The process of claim 1 wherein said detecting diagnoses *Bordetella* infection.

8. The process of claim 1 wherein said fourth amplification product is generated in parallel with said first amplification product.

9. The process of claim 1 wherein said detecting is by gel electrophoresis, Southern blotting, liquid chromatography, mass spectrometry, liquid chromatography/mass spectrometry, static fluorescence, dynamic fluorescence, high performance liquid chromatography, ultra-high performance liquid chromatography, enzyme-linked immunoadsorbent assay, real-time PCR, RT-PCR, nucleotide sequencing, or combinations thereof.

* * * * *

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: forward primer

<400> SEQUENCE: 1
caaggccgaa cgcttcat                                                 18

<210> SEQ ID NO 2
<211> LENGTH: 24
<212> TYPE: DNA
<213> ORGANISM: Artificial Sequence
<220> FEATURE:
<223> OTHER INFORMATION: reverse primer

<400> SEQUENCE: 2
gagttctggt aggtgtgagc gtaa                                          24

<210> SEQ ID NO 3
<211> LENGTH: 22
<212> TYPE: DNA
<213> ORGANISM: Artificial Sequence
<220> FEATURE:
<223> OTHER INFORMATION: probe

<400> SEQUENCE: 3
cagtcggcct tgcgtgagtg gg                                            22
```

```
<210> SEQ ID NO 4
<211> LENGTH: 20
<212> TYPE: DNA
<213> ORGANISM: Artificial Sequence
<220> FEATURE:
<223> OTHER INFORMATION: forward primer

<400> SEQUENCE: 4
ggcgacagcg agacagaatc                                                 20

<210> SEQ ID NO 5
<211> LENGTH: 17
<212> TYPE: DNA
<213> ORGANISM: Artificial Sequence
<220> FEATURE:
<223> OTHER INFORMATION: reverse primer

<400> SEQUENCE: 5
gccgccttgg ctcactt                                                    17

<210> SEQ ID NO 6
<211> LENGTH: 28
<212> TYPE: DNA
<213> ORGANISM: Artificial Sequence
<220> FEATURE:
<223> OTHER INFORMATION: probe

<400> SEQUENCE: 6
cgtgcagata ggcttttagc ttgagcgc                                        28

<210> SEQ ID NO 7
<211> LENGTH: 17
<212> TYPE: DNA
<213> ORGANISM: Artificial Sequence
<220> FEATURE:
<223> OTHER INFORMATION: forward primer

<400> SEQUENCE: 7
tcgaacgcgt ggaatgg                                                    17

<210> SEQ ID NO 8
<211> LENGTH: 20
<212> TYPE: DNA
<213> ORGANISM: Artificial Sequence
<220> FEATURE:
<223> OTHER INFORMATION: reverse primer

<400> SEQUENCE: 8
ggccgttggc ttcaaataga                                                 20

<210> SEQ ID NO 9
<211> LENGTH: 21
<212> TYPE: DNA
<213> ORGANISM: Artificial Sequence
<220> FEATURE:
<223> OTHER INFORMATION: probe

<400> SEQUENCE: 9
agacccaggg cgcacgctgt c                                               21

<210> SEQ ID NO 10
<211> LENGTH: 16
<212> TYPE: DNA
<213> ORGANISM: Artificial Sequence
<220> FEATURE:
<223> OTHER INFORMATION: primer
```

```
<400> SEQUENCE: 10
cgccagctcg tacttc                                                        16

<210> SEQ ID NO 11
<211> LENGTH: 15
<212> TYPE: DNA
<213> ORGANISM: Artificial Sequence
<220> FEATURE:
<223> OTHER INFORMATION: primer

<400> SEQUENCE: 11
gatacggccg gcatt                                                         15

<210> SEQ ID NO 12
<211> LENGTH: 22
<212> TYPE: DNA
<213> ORGANISM: Artificial Sequence
<220> FEATURE:
<223> OTHER INFORMATION: probe

<400> SEQUENCE: 12
aatacgtcga cacttatggc ga                                                 22
```